United States Patent [19]
Wasicek

[11] Patent Number: 5,989,218
[45] Date of Patent: *Nov. 23, 1999

[54] PERFUSION CATHETER WITH COIL SUPPORTED INNER TUBULAR MEMBER

[75] Inventor: Lawrence D. Wasicek, San Jose, Calif.

[73] Assignee: Advanced Cardiovascular Systems, Inc., Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/972,773

[22] Filed: Nov. 18, 1997

[51] Int. Cl.⁶ .................................................. A61M 25/00
[52] U.S. Cl. ........................... 604/96; 604/101; 604/102; 606/194
[58] Field of Search ............................. 604/96, 101, 102; 606/192–194

[56] References Cited

U.S. PATENT DOCUMENTS

| | | | |
|---|---|---|---|
| 3,938,529 | 2/1976 | Gibbons | 128/349 |
| 4,597,755 | 7/1986 | Samson et al. | 604/96 |
| 4,820,349 | 4/1989 | Saab | 606/194 |
| 4,944,745 | 7/1990 | Sogard et al. | 606/194 |
| 4,981,478 | 1/1991 | Evard et al. | 604/282 |
| 4,988,356 | 1/1991 | Crittenden et al. | 606/194 |
| 4,994,032 | 2/1991 | Sugiyama et al. | 604/96 |
| 5,141,518 | 8/1992 | Hess et al. | 606/194 |
| 5,176,637 | 1/1993 | Sagae | 604/96 |
| 5,195,971 | 3/1993 | Sirhan | 604/96 |
| 5,201,723 | 4/1993 | Quinn | 604/264 |
| 5,279,562 | 1/1994 | Sirhan et al. | 604/96 |
| 5,328,472 | 7/1994 | Steinke et al. | 604/102 |
| 5,344,402 | 9/1994 | Crocker | 604/96 |
| 5,383,890 | 1/1995 | Miraki et al. | 606/194 |
| 5,460,608 | 10/1995 | Lodin et al. | 604/96 |
| 5,492,532 | 2/1996 | Ryan et al. | 604/96 |
| 5,507,766 | 4/1996 | Kugo et al. | 606/194 |
| 5,516,336 | 5/1996 | McInnes e al. | 604/96 X |
| 5,542,925 | 8/1996 | Orth | 604/102 |
| 5,554,114 | 9/1996 | Wallace et al. | 604/53 |
| 5,573,509 | 11/1996 | Thornton | 604/102 |
| 5,591,129 | 1/1997 | Shoup et al. | 604/96 |
| 5,674,198 | 10/1997 | Leone | 604/101 |

FOREIGN PATENT DOCUMENTS

| | | |
|---|---|---|
| WO 93/01856 | 2/1993 | WIPO . |
| WO 93/13826 | 7/1993 | WIPO . |
| WO 93/21985 | 11/1993 | WIPO . |
| WO 97/32626 | 9/1997 | WIPO . |

*Primary Examiner*—John D. Yasko
*Attorney, Agent, or Firm*—Heller Ehrman White & McAuliffe

[57] ABSTRACT

A perfusion dilatation catheter is disclosed which has an improved distal catheter shaft portion with a tubular member extending within the balloon provided with an expanded coil support incorporated within the wall of the tubular member. The coil is preferably closer to the inner surface than the outer surface of the tubular member. Also disclosed are improved catheter shaft sections in a perfusion portion proximal to the balloon, one with a reinforced inflation tube depending into the guidewire lumen and another having three separate lumens, a central guidewire lumen and a pair of inflation lumens on opposing sides of the tubular structure defining the guidewire lumen.

8 Claims, 6 Drawing Sheets

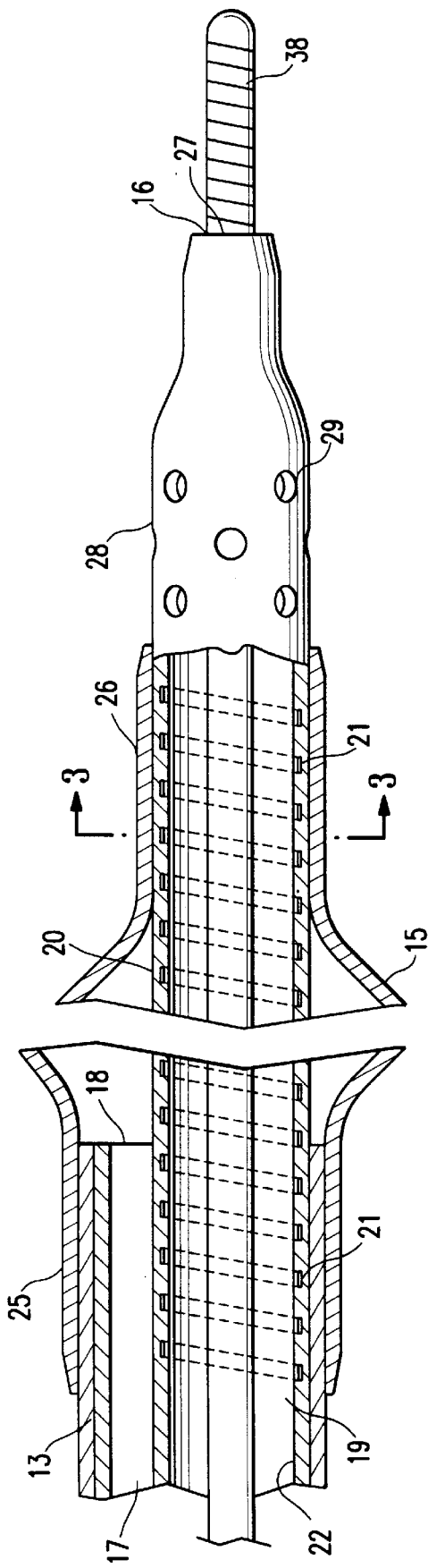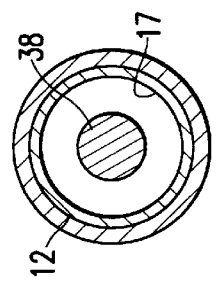

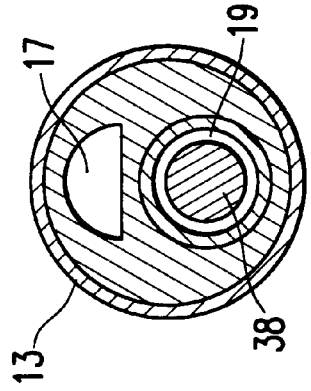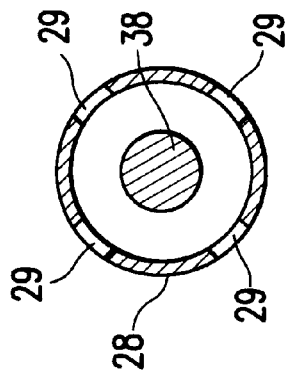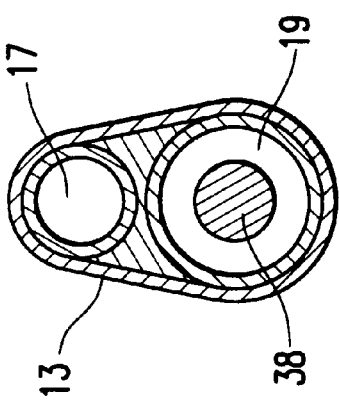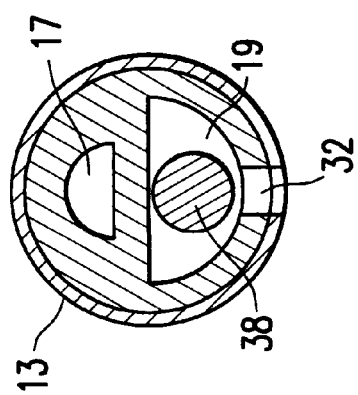

PERFUSION CATHETER WITH COIL SUPPORTED INNER TUBULAR MEMBER

BACKGROUND OF THE INVENTION

This invention generally relates to perfusion type intravascular catheters, particularly catheters for use in percutaneous transluminal coronary angioplasty (PCTA).

In a typical PTCA procedure a dilatation balloon catheter is advanced over a guidewire to a desired location within the patient's coronary anatomy where the balloon of the dilatation catheter is properly positioned within the stenosis to be dilated. The balloon is then inflated to a predetermined size with radiopaque liquid at relatively high pressures (generally 4–20 atmospheres) to dilate the stenosed region of the diseased artery. One or more inflations may be needed to effectively dilate the stenosis. The catheter may then be withdrawn from the stenosis or advanced further into the patient's coronary anatomy to dilate additional stenoses.

A high number of angioplasty procedures result in a dissected arterial lining which can collapse causing an acute closure of the arterial passageway. When an acute closure of the arterial passageway occurs, a perfusion device is usually advanced over the in-place guidewire to ensure adequate blood flow distal to the dissected lining until the lining be resecured to the artery wall or a by-pass procedure commenced. Preferably, a dilatation balloon catheter with perfusion capabilities is advanced over the in-place guidewire until the balloon crosses the dissection and then the balloon is inflated to press the dissected lining into place against the arterial wall. With the balloon inflated, blood is forced to pass through a perfusion passageway through the balloon to discharge the blood distal to the dissected arterial region. In this manner, the balloon remains in an inflated condition for sufficiently long periods of time, e.g. from about 0.5 to about 6 hours, for the natural healing process to resecure the dissected lining to the arterial wall.

Balloon dilatation catheters with perfusion capabilities have been available from Advanced Cardiovascular Systems, Inc. for a number of years, including the RX Perfusion and Lifestream Coronary Dilatation Catheters, which have met with much commercial success. Such catheters are described in U.S. Pat. No. 5,496,275 (Sirhan et al) an U.S. application Ser. No. 08/183,574, filed on Jan. 18, 1994 now U.S. Pat. No. 5,516,336 which are incorporated herein by reference in their entirety. The perfusion catheters presently on the market are predominantly rapid exchange type dilatation catheters due to the frequent need to advance a perfusion catheter over an in-place guidewire when an acute occlusion occurs after the original dilatation catheter has been deflated and withdrawn from the stenotic region.

Rapid exchange dilatation catheters with perfusion capabilities are more frequently being used as primary devices because if an arterial dissection does occur a perfusion catheter is already in place and all that is needed is to position the balloon within the dissected region and reinflate the balloon to cause the perfusion of oxygenated blood through the catheter and distal thereto and to hold the dissected lining against the arterial wall. However, with the advent of high pressure balloon use with rapid exchange type catheters, there is a tendency for the tubular member extending within the balloon to collapse, blocking the guidewire passageway. If the catheter is a perfusion type catheter, such a collapse blocks or at least restricts the passage of blood therethrough.

SUMMARY OF THE INVENTION

This invention is directed to a perfusion type balloon catheter which has a flexible distal shaft section with high perfusion flow rates.

The perfusion catheter of the invention generally has an elongated shaft with a proximal end, a distal end, a guidewire lumen extending through at least the distal section of the catheter and a port in the distal end in fluid communication with the guidewire lumen. The catheter also has an inflation lumen extending within the elongated shaft to a location spaced proximal to the distal end and an inflatable balloon on a distal section of the catheter shaft having an interior in fluid communication with the inflation lumen. The catheter shaft has a first plurality of perfusion ports in the distal section of the catheter located proximal to the distal end of the catheter and distal to the balloon which are in fluid communication with the guidewire lumen and a second plurality of perfusion ports in the distal section of the catheter located proximal to the balloon which are also in fluid communication with the guidewire lumen.

A tubular member extends through the interior of the balloon which has a wall with inner and outer surfaces with the inner surface defining at least a potion of the guidewire lumen extending therethrough. The wall of the tubular member is formed at least in part of a polymer matrix which extends between the inner and outer surface thereof. A supporting expanded coil, preferably formed of ribboned high strength material such as stainless steel or pseudoelastic or super elastic NiTi alloys, is disposed within the polymer matrix closer to the inner surface than the outer surface.

The supporting coil is preferably formed from a helically wound ribbon having long transverse cross-sectional dimension of about 0.003 to about 0.006 inch (mm) and a short transverse cross-sectional dimension of about 0.0005 to about 0.003 inch (mm). A rectangular transverse shape is preferred, although other oblong shapes such as oval or egg shapes may be employed. The coil is expanded with an inter-turn spacing of about 0.005 to about 0.020 inch (mm), preferably about 0.008 to about 0.015 inch (mm). The inter-turn spacing of the coils need not be constant, and, in fact, it is preferred to have the proximal portion of the coil to be expanded a greater degree than the distal portion.

To form the tubular member with an inner coil disposed therein, an expanded coil is mounted onto a supporting mandrel and polymeric shrink tubing is disposed over the mounted coil. Heat is applied to the shrink tubing to cause it to shrink onto and about the mounted expanded coil. The heated polymeric material flows about the coil, between the expanded turns thereof and provides a smooth inner polymer surface which defines the guidewire lumen extending through the tubular member. The polymeric material of the tubular member is a relatively inelastic polymer such as high density polyethylene or polyetheretherketon (PEEK) and with the coil support therein there is little or no tendency for the tubular member to collapse upon the introduction of high pressure inflation fluid into the interior of the balloon.

The length of the distal shaft section having the first plurality of perfusion ports is relatively short and generally is less than three mm, preferably less than 2 mm. The perfusion ports in this distal section of the catheter are aligned circumferentially in at least two rows, and preferably are about 0.01 to about 0.02 mm in maximum dimension. The rows of circumferentially disposed perfusion ports are longitudinally spaced from each other about 0.2 to about 0.4 mm, preferably about 0.25 to about 0.35 mm. The length of the distal portion of the catheter having the first plurality of perfusion ports may be tapered distally from larger to smaller outer dimensions. Preferably, the circumferentially disposed perfusion ports typically should be arranged in rows with about 2 to about 4 ports per row. The number of ports per row may decrease in the distal direction, e.g. the first row(s) may have four ports and the more distally positioned rows may have 3 ports. The ports in adjacent rows can be longitudinally aligned with each other but are preferably staggered.

These and other advantages of the invention will become more apparent from the following detailed description of the invention when taken in conjunction with the accompanying exemplary drawings.

BRIEF DESCRIPTION OF THE DRAWINGS

FIG. 2 is an enlarged longitudinal cross-sectional view of a distal portion of the catheter shown in FIG. 1 taken along the lines 2—2.

FIG. 3 is a transverse cross-sectional view of the distal portion of the catheter as shown in FIG. 2 taken along the lines 3—3.

FIG. 4 is a transverse cross-sectional view of the catheter shown in FIG. 1 taken along the lines 4—4.

FIG. 5 is a transverse cross-sectional view of the catheter shown in FIG. 1 taken along the lines 5—5.

FIG. 6 is a transverse cross-sectional view of the catheter shown in FIG. 1 taken along the lines 6—6.

FIG. 7 is a transverse cross-sectional view of the catheter shown in FIG. 1 taken along the lines 7—7

FIG. 8 is a transverse cross-sectional view of the catheter shown in FIG. 1 taken along the lines of 8—8.

DETAILED DESCRIPTION OF THE INVENTION

Figure 1:
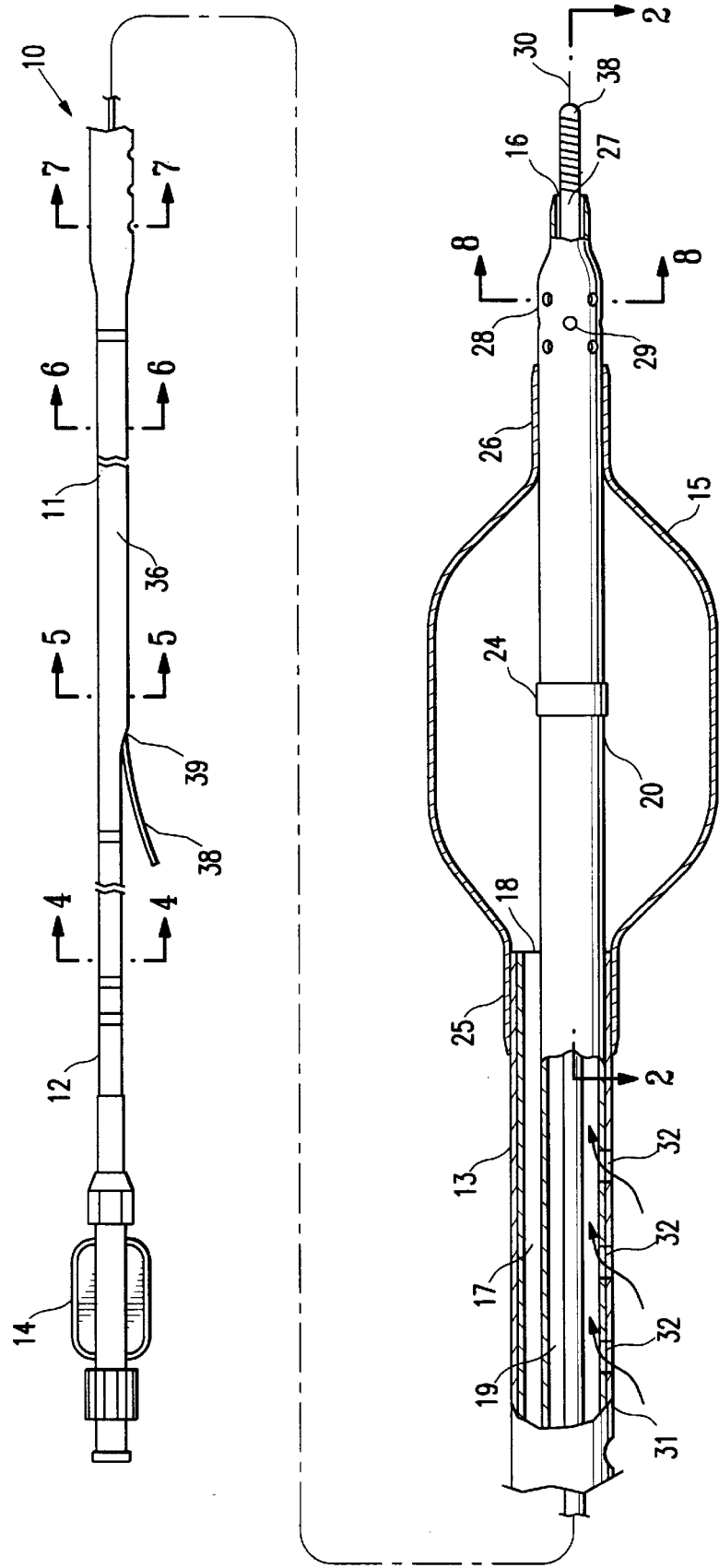
FIG. 1 is an elevational view, partially in section, of a rapid exchange or rail type perfusion dilatation catheter embodying features of the invention.

Reference is made to FIGS. 1–8 which schematically illustrate perfusion dilatation catheter 10 embodying features of the invention. The catheter 10 has an elongated shaft 11 with proximal and distal shaft sections 12 and 13, an adapter 14 on the proximal end of the shaft and a dilatation balloon 15 on the distal shaft section spaced proximal to the distal end 16. An inflation lumen 17 extends between the proximal end of shaft 11 and a location 18 spaced proximal to the distal end 16 and is in fluid communication with the interior of the dilatation balloon 15. A guidewire receiving lumen 19 extends within the distal shaft section 13 and is defined at least in part by an inner tubular member 20 which extends through the interior of the balloon 15.

The inner tubular member 20, as shown in more detail in FIGS. 2 and 3, is provided with an inner coil member 21 which is disposed closer to the inner surface 22 of the inner tubular member than the outer surface 23. As best shown in FIG. 2, the coil 21 is expanded to provide a spacing between the turns which should range from about 0.005 to about 0.03 inch (0.13–0.76 mm), preferably about 0.01 to about 0.025 inch (0.25–0.64 mm). A single radiopaque marker 24 is provided at a mid-balloon position on the inner tubular member 20. Multiple markers may be mounted on the inner tubular member 20 underneath each end of the cylindrical portion of the balloon, i.e. the working length of the balloon, to facilitate fluoroscopic observation of the working length of the balloon during the procedure.

The balloon 15 has a proximal skirt 25 which is secured to the distal end of the catheter shaft 11 and a distal skirt 26 which is secured to the distal extremity of the inner tubular member 20. The tubular member 20 forms the guidewire lumen 19 to the distal port 27 in the distal end 16 of the catheter. Distal perfusion portion 28 of the distal shaft section 13 is formed at least in part by the distal portion of the inner tubular member 20 which is preferably tapered distally from a larger diameter to a smaller diameter as shown. The distal perfusion portion 28 has multiple rows of three or four perfusion ports 29 which are disposed circumferentially about the longitudinal axis 30 of the catheter shaft 11.

Figure 9:
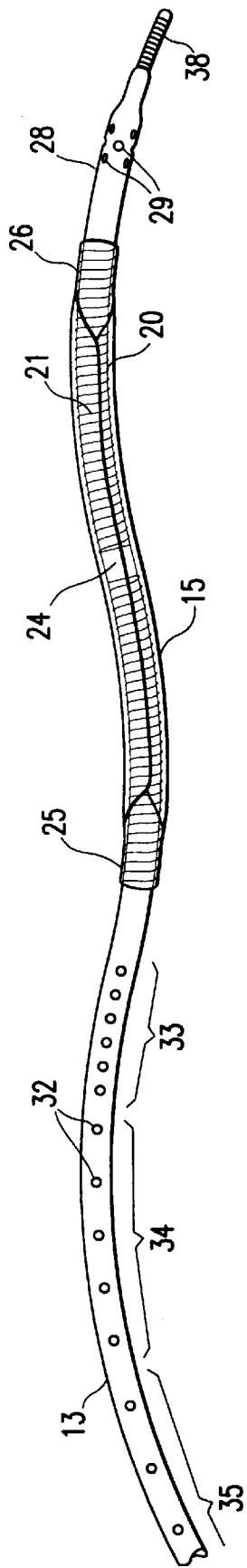
FIG. 9 is an elevational view of a distal extremity of the catheter shown in FIGS. 1–8 with a transparent wrapped balloon.

A proximal perfusion portion 31 of the distal shaft section 13 is located proximal to the balloon 15 and typically has about 8 to about 20 perfusion ports 32 which extend through the wall of the proximal perfusion portion 31. As shown in FIG. 9, the proximal perfusion ports 32 are arranged into groups having different spacings, with the most distal group 33 of perfusion ports having the smallest interport spacing, the intermediate group 34 having an intermediate interport spacing and the most proximal group 35 having the greatest interport spacing. While a plurality of ports 32 are depicted in the drawing in each group, one or more elongated perfusion ports can be employed to replace a plurality of ports in each group of the proximal perfusion portion 31. The proximal perfusion portion 31 of the distal shaft section 13 is typically about 2 to about 35 cm, preferably about 10 to about 25 cm, in length. The outer diameter of the proximal perfusion portion is desirably about 3 to about 4 French (1–1.4 mm).

The proximal non-perfusion portion 36 of the distal shaft section 13 proximal to the proximal perfusion portion 31 is about 0.5 French (0.16 mm) smaller in diameter than the proximal perfusion portion. This distal section may be formed by fusing together inner and outer tubular members (not shown) into the shape indicated by inserting mandrels of the desired shapes for the guidewire lumen 19 and the inflation lumen 17 during the fusion process which is described in co-pending application Ser. No. 08/742,689, filed on Nov. 4, 1996, which is incorporated herein by reference in its entirety.

The balloon 15 is of conventional structure and may be from 1 to 10 cm in length and from 1 to 4.5 mm in inflated diameter. The balloon material may be selected from conventional materials such as polyethylene, nylon, polyethylene terephthalate and the like.

The guidewire 38 extends through the guidewire receiving lumen 19 from the proximal port 39 to the distal port 27 in the distal end 16 of the catheter shaft 11. The proximal port 39 is spaced at least about 15 to about 35 cm from the distal end 16 of the catheter shaft 11. A slit (not shown) may extend from the proximal port 39 to a location proximal to the proximal perfusion portion 31 of the distal shaft section 13 to facilitate removal of the catheter from the guidewire when withdrawing the catheter from the patient.

Figure 11:
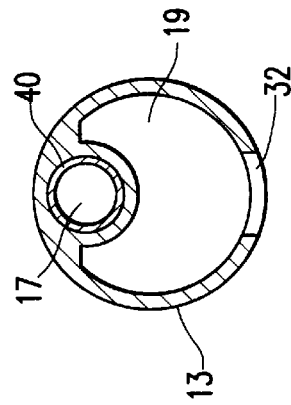
FIG. 11 is a transverse cross-sectional view of the catheter shaft structure shown in FIG. 10, taken along the lines 11—11.
Figure 10:
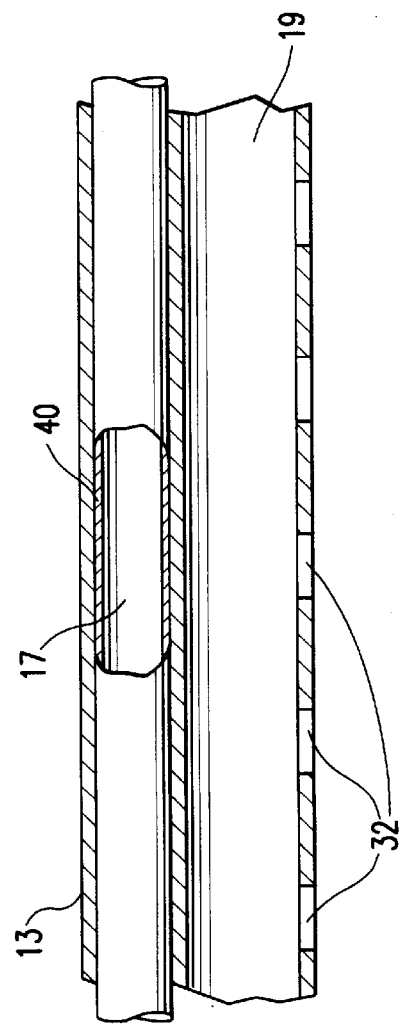
FIG. 10 is a partial elevational view, partially in section, of an alternative catheter shaft structure which may be used in the proximal perfusion portion of the catheter.

The proximal perfusion portion 31 and the proximal non-perfusion portion 36 of the distal shaft section 13, as best shown in FIGS. 5–7, basically has a dual lumen construction with a variety of lumen sizes and shapes. Alternative construction may be employed. For example, the proximal perfusion portion 31 may have a tubular member 40 defining the inflation lumen 17 which depends into the guidewire lumen 19 as shown in FIGS. 10 and 11. The tubular member 40 may be made of suitable high strength materials such a stainless steel, NiTi alloys, polyetheretherketone (PEEK) and polyimide. This design provides for a larger perfusion lumen and reduced overall profile for this catheter section.

Figure 13:
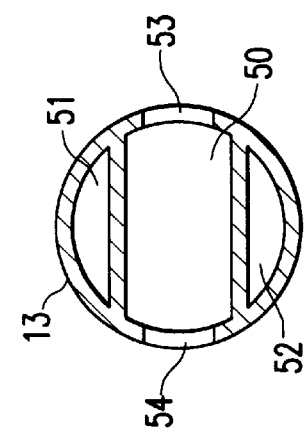
FIG. 13 is a transverse cross-sectional view of the catheter shaft structure shown in FIG. 12, taken along the lines 13—13.
Figure 12:
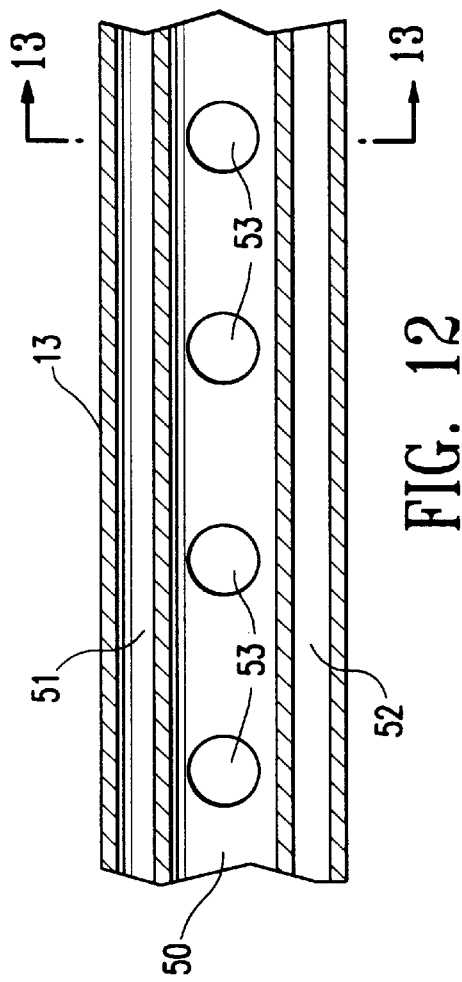
FIG. 12 is a partial elevational view, partially in section, of an alternative catheter shaft structure which may be used in the perfusion portion of the catheter.

Another alternative proximal perfusion portion 31 is shown in FIGS. 12 and 13 which has a triple lumen construction, a central guidewire lumen 50 and a pair of inflation lumens 51 and 52 with circular sector shaped transverse cross-sections. Perfusion ports 53 and 54 may be provided in both sides of the guidewire lumen 50, thereby increasing perfusion flow rates.

Figure 14:
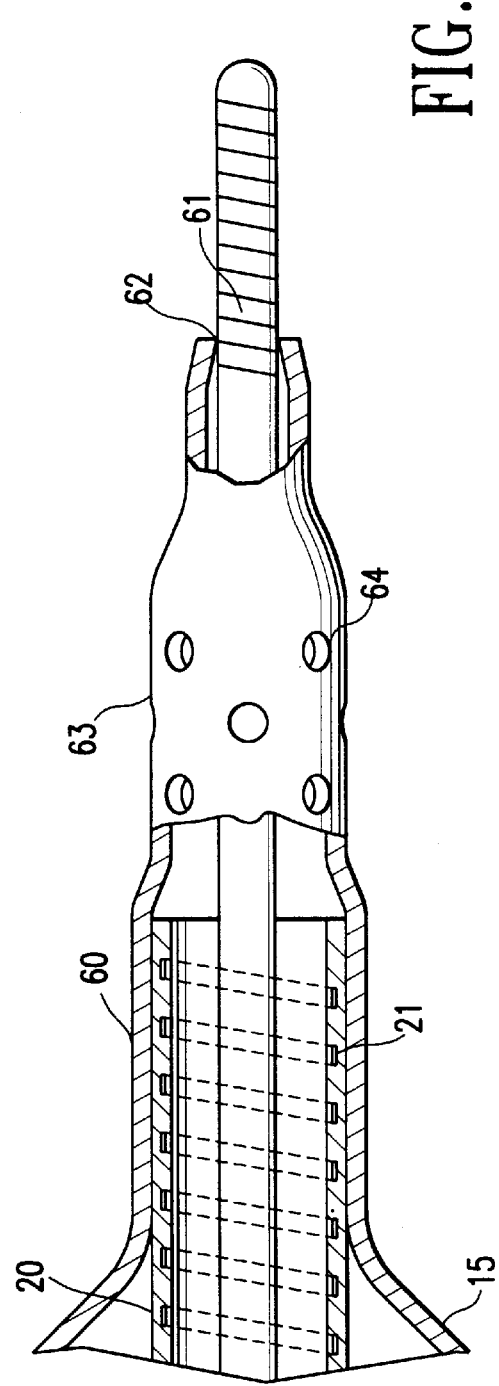
FIG. 14 is an elevational view, partially in section, of an alternative catheter construction in which the distal skirt of the balloon forms the distal perfusion portion of the catheter.

An alternative catheter construction is shown in FIG. 14 wherein the distal skirt 60 of the balloon 15 extends beyond the distal end of the inner tubular member 20 to the distal port 61 in the distal end 62 and forms the cylindrically shaped distal perfusion portion 63 of the distal shaft section 13. A plurality of rows of three or four perfusion ports 64 are provided in the wall of the cylindrically shaped distal perfusion portion 63.

Figure 15:
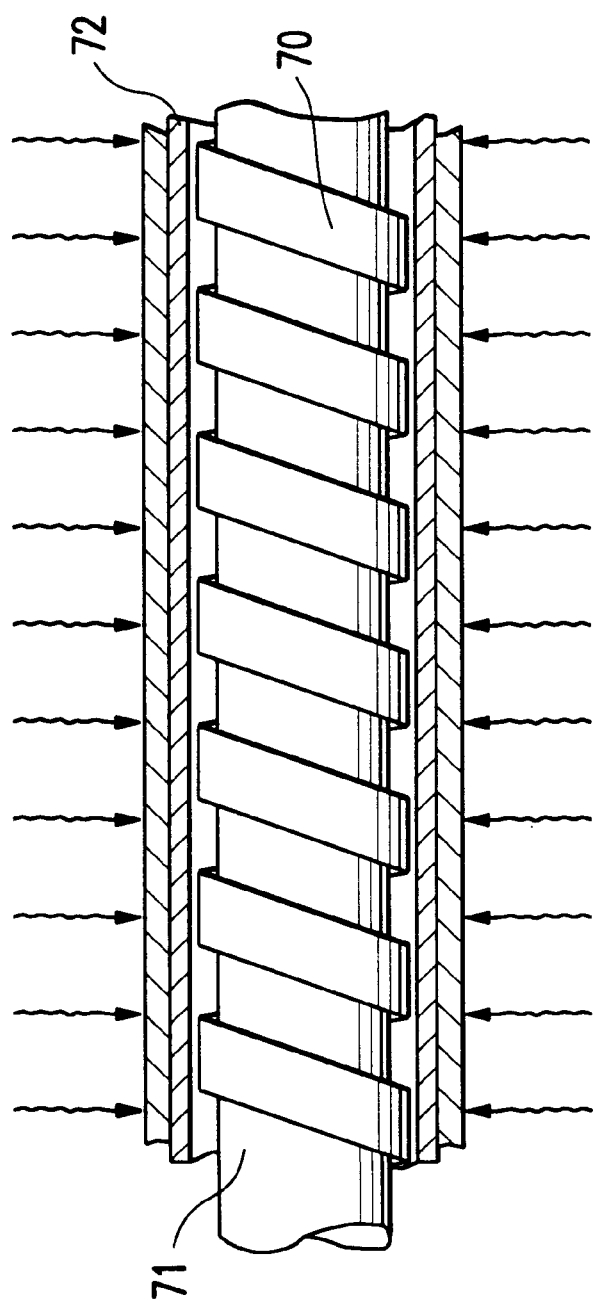
FIG. 15 is a schematic view demonstrating the manufacture of the inner tubular member shown in FIG. 2.

The coil reinforced inner tubular member 20 is presently formed by placing the coil 70 on a suitable sized mandrel 71, surrounding the coil with a polymeric tube 72 and then placing a polymeric shrink tube 73 about the polymeric tube. The shrink tube 73 is heat shrunk as indicated in FIG. 15. forcing the polymeric material of the polymeric tube 72 into the coil 70.

To the extent not described herein or in any of the U.S. patents or patent applications which have been incorporated herein by reference, the dimensions, structural details and materials of construction may follow conventional practice for intravascular catheters such as balloon dilatation catheters used in angioplasty procedures. Moreover, various changes and modification may be made to the present invention without departing from the scope of the invention. Additionally, although individual features of the several embodiments of the invention may be shown in some of the drawings and not in others, those skilled in the art will recognize that individual features of one embodiment of the invention can be combined with the features of another embodiment.

What is claimed is:

1. A perfusion balloon catheter configured for slidable movement over a guidewire, comprising:

a) an elongated catheter shaft having a proximal end, a distal end, a port in the distal end larger in transverse dimensions than transverse dimensions of the guidewire, a guidewire lumen extending within the elongated catheter shaft in fluid communication with the port in the distal end, an inflation lumen extending within the catheter shaft to a location spaced proximal to the distal end;

b) a balloon on a distal shaft section of the elongated catheter shaft having an interior in fluid communication with the inflation lumen;

c) a proximal portion of the distal shaft section which has a plurality of longitudinally disposed perfusion ports located proximal to the balloon in fluid communication with the guidewire lumen;

d) a cylindrically shaped distal portion of the distal shaft section located distal to the balloon; having a plurality of perfusion ports spaced proximal to the distal end in fluid communication with the guidewire lumen; and e) a tubular member which extends through the interior of the inflatable balloon, which has a wall defining at least a portion of the guidewire lumen extending therein with inner and outer surfaces and a polymer matrix therebetween, which has an expanded helical metallic ribbon coil incorporated within the polymer matrix having an interturn spacing of about 0.005 to about 0.030 inch (0.1–0.76 mm) and which has a distal extremity secured to the distal skirt of the balloon.

2. The perfusion balloon catheter of claim 1 wherein the helical coil is closer to the inner surface than the outer surface of said wall.

3. The perfusion balloon catheter of claim 2 wherein the long transverse dimensions of the ribbon material of the coil is about 0.003 to about 0.006 inch.

4. The perfusion balloon catheter of claim 2 wherein the short transverse dimensions of the ribbon material of the coil is about 0.0005 to about 0.003 inch.

5. The perfusion balloon catheter of claim 1 wherein the inner tubular member has a wall thickness of at least 20% greater than the short transverse dimension of the ribbon material.

6. The perfusion balloon catheter of claim 1 wherein the inner tubular member has a wall thickness of at least 50% greater than the short transverse dimension of the ribbon material.

7. The perfusion balloon catheter of claim 1 wherein the proximal perfusion portion of the distal section has a high strength tubular element defining the inflation lumen which is disposed within a wall portion of the proximal perfusion portion with said wall portion in part depending into the guidewire lumen.

8. The perfusion balloon catheter of claim 1 wherein the proximal perfusion portion of the distal section has three lumens, a centrally disposed guidewire lumen and a pair of inflation lumens on opposing sides of the guidewire lumen.

* * * * *

UNITED STATES PATENT AND TRADEMARK OFFICE
Certificate

Patent No. 5,989,218                                                         Patented: November 23, 1999

On petition requesting issuance of a certificate for correction of inventorship pursuant to 35 U.S.C. 256, it has been found that the above-identified patent, through error and without deceptive intent, improperly sets forth the inventorship.

Accordingly, it is hereby certified that the correct inventorship of this patent is: Lawrence D. Wasicek; Yen Chan Mina; W. B. Chow; Ketan P. Muni; Bonzena Z. Maslanka.

Signed and Sealed this Twenty-fourth Day of April, 2001.

*RICHARD SEIDEL*
*Supervisory Patent Examiner*
Art Unit 3763

UNITED STATES PATENT AND TRADEMARK OFFICE
Certificate

Patent No. 5,989,218  Patented: November 23, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Lawrence D. Wasicek, San Jose, CA; Yen Chan, San Jose, CA; Mina W. B. Chow, Campbell, CA; Ketan P. Muni, San Jose, CA; and Bozena Z. Maslanka, Santa Cruz, CA.

Signed and Sealed this Fourteenth Day of August, 2001.

RICHARD SEIDEL
*Supervisory Patent Examiner*
Art Unit 3763

UNITED STATES PATENT AND TRADEMARK OFFICE
Certificate

Patent No. 5,989,218

Patented: November 23, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Lawrence D. Wasicek, San Jose, CA; Yen Chan, San Jose, CA; Yen Chan, San Jose, CA; Mina W.B. Chow, Campbell, CA; Ketan P. Muni, San Jose, CA; Bozena Z. Maslanka, Santa Cruz, CA; Sergio Correa, Encinitas, CA; and Richard J. Saunders, Redwood City, CA.

Signed and Sealed this Thirteenth Day of January 2004.

BRIAN L. CASLER
*Supervisory Patent Examiner*
*Art Unit 3763*

UNITED STATES PATENT AND TRADEMARK OFFICE
Certificate

Patent No. 5,989,218

Patented: November 23, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Lawrence D. Wasicek, San Jose, CA; Yen Chan, San Jose, CA; Mina W.B. Chow, Campbell, CA; Ketan P. Muni, SanJose, CA; Bozena Z. Maslanka, Santa Cruz, CA; Sergio Correa, Encinitas, CA; and Richard J. Saunders, Redwood City, CA.

Signed and Sealed this Twenty-eighth Day of December 2004.

BRIAN L. CASLER
*Supervisory Patent Examiner*
Art Unit 3763